United States Patent [19]

Larkin

[11] 4,124,608

[45] Nov. 7, 1978

[54] PREPARATION OF 2-OXOALKANOIC ACIDS

[75] Inventor: John M. Larkin, Austin, Tex.

[73] Assignee: Texaco Inc., New York, N.Y.

[21] Appl. No.: 821,435

[22] Filed: Aug. 3, 1977

[51] Int. Cl.$^2$ .................... C09F 5/00; C11C 3/00; C11C 1/00

[52] U.S. Cl. .................... 260/405; 260/413; 260/465.1; 562/577

[58] Field of Search .............. 260/405, 413 R, 413 Q, 260/514 K, 535 R, 469.1

[56] References Cited

U.S. PATENT DOCUMENTS 3,518,302   6/1970   Ellis .................... 260/413 R 4,058,541   11/1977   Kablaoui .................... 260/535 R

OTHER PUBLICATIONS

Chem. Rev. 41, pp. 585–598 (1947).

*Primary Examiner*—Winston A. Douglas
*Assistant Examiner*—John F. Niebling
*Attorney, Agent, or Firm*—Thomas H. Whaley; Carl G. Ries; George J. Darsa

[57] ABSTRACT

2-oxoalkanoic acids are prepared by contacting an alpha-nitroketone with an alkanoic acid anhydride, such as acetic anhydride, and a tertiary amine, such as pyridine, thereby forming a 2-alkanoyloxy-2-alkenoic acid and thereafter hydrolyzing the alkenoic acid with an aqueous non-oxidizing acid, such as hydrochloric acid.

35 Claims, No Drawings

PREPARATION OF 2-OXOALKANOIC ACIDS

BACKGROUND OF THE INVENTION

This invention relates to a method for preparing 2-oxoalkanoic acids. In particular, this invention relates to a method of preparing 2-oxoalkanoic acids from alpha-nitroketones.

The preparation of oxoalkanoic acids or keto acids has been described by Walters, Chem. Rev. 41, 585–598 (1947). One method for the preparation of the acids involves initially reacting an acyl halide and a metal cyanide to form an acyl cyanide. The acyl cyanide is thereafter hydrolyzed to the keto acid. This procedure, however, is said to be inapplicable for obtaining keto acids having more than five carbon atoms. Another method involves hydrolysis of an oxime ester. In this procedure, to an oxime dissolved in formic acid and maintained at 0° C., is added nitrosyl sulfuric acid. However, it is reported that the conversion from the oxime to keto acid is generally poor and the method is not applicable to the preparation of all keto acids. Yet another method involves refluxing a fatty acid ester, diethyl oxalate, and sodium ethoxide in ether thereby forming an oxaloester. The oxaloester is subsequently treated with boiling dilute sulfuric acid to obtain the keto acid. In those instances where longer chain keto acids were desired, such as those having 10 or more carbons, the method was conducted for a period of 100 hours. One further method involves hydrolysis of the addition product of Grignard reagents and diethyloxamates at very low temperatures. The preparation of diethyloxamates is said to have occurred over a tediously long refluxing time. It is apparent, therefore, that each of the aforementioned methods suffer serious disadvantages including the inability to produce substantial amounts of higher keto acids or the necessity to conduct the process over extended periods of time.

It is therefore an object of this invention to provide a novel method for the preparation of 2-oxoalkanoic acids.

It is another object of this invention to provide a method for the preparation of 2-oxoalkanoic acids in good yields.

Yet another object of this invention is to provide a method for the preparation of 2-oxoalkanoic acids from materials having long storage lives.

Other objects and advantages will become apparent from the following detailed description and examples.

SUMMARY OF THE INVENTION

Broadly this invention contemplates a method for the preparation of a 2-oxoalkanoic acid which comprises contacting an alpha-nitroketone with an alkanoic acid anhydride and a tertiary amine thereby forming a 2-alkanoyloxy-2-alkenoic acid and hydrolyzing the alkenoic acid with an aqueous non-oxidizing inorganic or organic acid.

According to this invention, the alpha-nitroketones contemplated as starting material in the instant invention correspond to the formula:

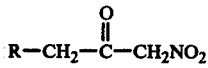

$$R-CH_2-\overset{\overset{O}{\|}}{C}-CH_2NO_2$$

where R is hydrogen or an alkyl group having from 1 to 50 carbon atoms, and where R is preferably an alkyl group of 5 to 20 carbon atoms. Illustrative of the alpha-nitroketones contemplated herein can be mentioned 1-nitro-2-propanone, 1-nitro-2-butanone, 1-nitro-2-pentanone, 1-nitro-4-methyl-2-pentanone, 1-nitro-2-hexanone, 1-nitro-2-heptanone, 1-nitro-2-octanone, 1-nitro-2-decanone, 1-nitro-2-dodecanone, 1-nitro-2-pentadecanone, 1-nitro-2-hexadecanone, 1-nitro-2-heptadecanone, 1-nitro-2-eicosanone, and 1-nitro-2-heneicosanone.

More specifically, the overall process of the invention will be apparent from the following stages:

Stage 1. The first stage of the method comprises reacting an alpha-nitroketone as hereinabove described with an alkanoic acid anhydride of the formula (R'CO)$_2$O where R' is an alkyl group of 1 to 11 carbons and illustrated by ethanoic anhydride (acetic anhydride), propanoic anhydride, butanoic anhydride, pentanoic anhydride, hexanoic anhydride, octanoic anhydride, decanoic anhydride and dodecanoic anhydride, preferably acetic anhydride. The contacting of the alpha-nitroketone and anhydride is undertaken in the presence of a catalyst, namely a tertiary amine, thereby forming a 2-alkanoyloxy-2-alkenoic acid corresponding to the formula:

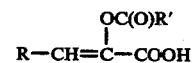

$$R-CH=\overset{\overset{OC(O)R'}{|}}{C}-COOH$$

where R and R' are as described above.

In general, the first stage reaction can be undertaken employing mole ratios of nitroketone to alkanoic acid anhydride of from about 1:1 to about 1:20, preferably 1:2 to about 1:15. In general, amounts of anhydride in excess of that needed to stoichiometrically react with the nitroketone can be utilized with the excess anhydride functioning as the reaction medium. A solvent can also be employed if desired. Typical solvents include any nonreactive solvents possessing a boiling point of about 30° to 150° C., such as benzene, cyclohexane, toluene, tetrahydrofuran, diethylether, n-octane, chloroform, carbon tetrachloride, 1,4-dioxane and chlorobenzene.

As mentioned above, the first stage of the method is conducted in the presence of a tertiary amine catalyst. Suitably, mole ratios of nitroketone to tertiary amine range from about 1:0.5 to 1:50, preferably from about 1:0.5 to 1:5. The amine when present in substantial amounts, that is at mole ratios of nitroketone to amine of 1:1 to 1:50 may also function as the reaction medium.

The contacting of the reactants in the first stage can be undertaken at from about room temperature to about 150° C. At temperatures below about room temperature, the reaction is excessively slow and at temperatures exceeding about 150° C., the method provides substantially diminished yields of desired acid. Further, when operating within the temperatures described above and particularly at the higher temperatures, such as about 90° to 150° C., substantial amounts of alkylnitrile as a coproduct is formed corresponding to the formula RCH$_2$CN, where R is as defined above. Representative alkylnitriles formed as coproduct include propionitrile, pentanonitrile, heptanonitrile, nonanonitrile, undecanonitrile, tridecanonitrile and pentadecanonitrile. It will be appreciated that the alkylnitrile formed in the first stage, when the method is conducted at the higher temperatures, contains one fewer carbon than the starting nitroketone material.

The tertiary amines contemplated as catalyst in the first stage of the method include alkyl, cycloalkyl, aryl or heterocyclic amines having 3 to 36 carbons. Illustrative amines include N-butyldidodecylamine, N,N-diethylcyclohexylamine, N,N-diethyldodecylamine, N,N-dimethylaniline, N,N-dimethylbenzylamine, N,N-dimethyloctylamine, N,N-diisopropylethylamine, N,N-dimethylethylamine, N,N-diethylmethylamine, N,N-dimethylpropylamine, N,N-diethylpropylamine, N,N-ethylmethylpropylamine, N-ethyldibenzylamine, tributylamine, tridodecylamine, triethylamine, trihexylamine, trimethylamine, tricyclohexylamine, pyridine, N-methylpiperidine, 2-ethylpyridine, 1,4-dimethylpiperazine, 4-ethylpyridine, 2,4-lutidine, 3-picoline, 2,4,6-trimethylpyridine, and quinoline. The preferred tertiary amines are pyridine, quinoline and triethylamine.

Illustrative of the 2-alkanoyloxy-2-alkenoic acids prepared in the first stage, I mention 2-ethanoyloxy-2-butenoic acid, 2-propanoyloxy-2-hexenoic acid, 2-butanoyloxy-2-octenoic acid, 2-pentanoyloxy-2-decenoic acid, 2-hexanoyloxy-2-dodecenoic acid, 2-octanoyloxy-2-tetradecenoic acid, 2-decanoyloxy-2-hexadecenoic acid, 2-ethanoyloxy-2-octenoic acid, 2-ethanoyloxy-2-decenoic acid, 2-ethanoyloxy-2-dodecenoic acid and 2-ethanoyloxy-2-hexadecenoic acid.

The 2-alkanoyloxy-2-alkenoic acids prepared above, may be recovered and separated from the first stage reaction product by vacuum distillation. Unreacted anhydride can also be separated by vacuum distillation and recycled for reintroduction to the first stage as can the tertiary amine. Fractional crystallization from hydrocarbon solvents such as n-pentane, n-hexane and the like can also be employed.

Alternately, the entire reaction mixture can be treated with water containing sodium hydroxide or sodium carbonate thereby hydrolyzing unreacted anhydride to a carboxylic acid. The solution can thereafter be extracted with a water-immiscible organic solvent, such as diethylether, to extract the tertiary amine. The 2-alkanoyloxy-2-alkenoic acid, carboxylic acid and alkylnitrile coproduct when formed can be separated by fractional distillation at reduced pressure or by fractional crystallization, the latter being preferred in the instance where higher molecular weight alkenoic acids are prepared.

Stage 2. The 2-alkanoyloxy-2-alkenoic acid prepared above, is converted to a 2-oxoalkanoic acid by contacting with an aqueous non-oxidizing inorganic or organic acid at a temperature of from about 80° to 100° C. The non-oxidizing acids contemplated in this stage have a pka of about 4.0 to 0.25, preferably about 2.0 to 0.25. Suitable non-oxidizing inorganic acids include dilute hydrochloric acid, sulfuric acid, phosphoric acid, phosphorous acid, pyrophosphoric acid, perchloric acid and hydrobromic acid. Typical non-oxidizing organic acids can be illustrated by methanesulfonic acid, p-toluenesulfonic acid, m-toluenesulfonic acid, p-bromobenzenesulfonic acid, p-chlorobenzenesulfonic acid, 2,6-naphthalenedisulfonic acid, 1-naphthalenesulfonic acid, 2-naphthalenesulfonic acid, benzenesulfonic acid, 2-mesitylenesulfonic acid, 2-dodecylphenylsulfonic acid, p-nitrobenzoic acid, m-nitrobenzoic acid, 2-methyl-4-nitrobenzoic acid, 2-butyl-4-nitrobenzoic acid, p-nitrophenylacetic acid, chloroacetic acid, dichloroacetic acid, trichloroacetic acid, dichloropropanoic acid and dichlorobutanoic acid. The non-oxidizing acid is generally employed in this stage of the method in amounts ranging from about 0.1 to 20 moles of non-oxidizing acid per mole of 2-alkanoyloxy-2-alkenoic acid. Preferably, hydrochloric acid is employed. Oxidizing acids, such as nitric acid, are inappropriate in that they promote the formation of tars and resins. Further, the second stage of the method involving hydrolysis of the 2-alkanoyloxy-2-alkenoic acid to a 2-oxoalkanoic acid is preferably conducted in the presence of a non-reactive polar organic solvent having a boiling point of at least about 80° C. and up to about 180° C. Illustrative solvents include dioxane, acetic acid, dimethylformamide, acetonitrile, monomethylether of diethylene glycol, isopropanol and n-butanol. Solvents such as hydrocarbons are not favored inasmuch as the desired reaction is extremely slow and water is difficultly soluble therein.

The second stage reaction described above forms 2-oxoalkanoic acids corresponding to the formula:

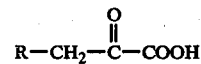

where R is as defined above. Illustrative of the oxoalkanoic acids provided by the method can be mentioned 2-oxoproprionic acid, 2-oxobutanoic acid, 2-oxohexanoic acid, 2-oxooctanoic acid, 2-oxodecanoic acid, 2-oxododecanoic acid, 2-oxotridecanoic acid, 2-oxotetradecanoic acid, 2-oxohexadecanoic acid and 2-oxooctadecanoic acid. At the completion of the second stage reaction, the oxoalkanoic acid can be recovered by extraction of the solution with a water immiscible organic solvent, such as diethylether, benzene or chloroform and separation of the solvent by fractionation or evaporation.

The 2-oxoalkanoic acids prepared by the method described above are useful in the electrodeposition of stress-free metal deposits and may be used as components of a bath for the electrodeposition of such metals as nickel, cobalt, zinc or copper and described in U.S. Pat. No. 3,338,804. The oxo acids are also useful as corrosion inhibitors in fuels and lubricants and as intermediates in the preparation of other valuable products as alkylnitriles by reaction with hydroxylamine hydrochloride at reflux in water as described in the Canadian Journal of Chemistry, Volume 39, pages 1340–1359 (1961).

In order to more fully illustrate the nature of this invention and the manner of practicing the same, the following examples are presented.

EXAMPLE 1

A solution of 5.0 grams (0.0175 mole) of 1-nitro-2-hexadecanone, 0.2 milliliters (0.025 mole) of pyridine and 18 milliliters (0.191 mole) of acetic anhydride was heated at reflux for four hours. After cooling, the mixture was poured into 75 milliliters of ice water, stirred and extracted with two 200 milliliter portions of diethylether. The ethereal extracts were washed with two 50 milliliter portions of saturated sodium bicarbonate solution, 75 milliliters of 1.2 N HCl, 50 milliliters of water and finally with 50 milliliters of a saturated sodium chloride solution. The ether solution was dried, the solvent evaporated under vacuum and a residue of 2.67 grams was recovered.

The above procedure was repeated except that 36 milliliters (0.38 mole) of acetic anhydride, 0.4 milliliters (0.05 mole) of pyridine and 10.0 grams (0.04 mole) of 1-nitro-2-hexadecanone were employed and 9.35 grams of residue was obtained.

After combining the above residues and upon recrystallization, 4.71 grams of material was recovered and identified upon analysis to be 2-ethanoyloxy-2-hexadecenoic acid (2-acetoxy-2-hexadecenoic acid). In addition, 2.38 grams of a coproduct was recovered and indicated by analysis to be pentadecanonitrile.

EXAMPLE 2

A mixture of 3.0 grams (0.01 mole) of 1-nitro-2-hexadecanone, 10.0 milliliters (0.01 mole) of acetic anhydride and 0.2 milliliters (0.03 mole) of pyridine were stirred at room temperature and the resulting brown liquid added to 50 milliliters of ice water and stirred for three hours. The mixture, following extraction, provided a residue weighing 3.7 grams which upon analysis was identified to be 2-ethanoyloxy-2-hexadecenoic acid.

EXAMPLE 3

A solution of 0.78 grams (0.003 mole) of 2-ethanoyloxy-2-hexadecenoic acid, 1 milliliter of water, 1 milliliter of 12 N HCl and 10 milliliters of dioxane was heated at reflux (89° C.). The solution was diluted with 100 milliliters of water, filtered and again washed in water. A solid product weighing 0.41 grams was recrystallized from chloroform and identified by infrared analysis to be 2-oxohexadecanoic acid.

I claim:

1. A method for the preparation of a 2-oxoalkanoic acid which comprises:
    (a) contacting an alpha-nitroketone with an alkanoic acid anhydride and a tertiary amine thereby forming a 2-alkanoyloxy-2-alkenoic acid, and
    (b) hydrolyzing said alkenoic acid with an aqueous non-oxidizing inorganic or organic acid.

2. A method according to claim 1 wherein said contacting in step (a) is conducted at a temperature of from about room temperature to 150° C.

3. A method according to claim 1 wherein said contacting in step (a) is conducted at a temperature of from about 90° to 150° C. and where an alkylnitrile coproduct is formed.

4. A method according to claim 1 wherein the mole ratio of said nitroketone to said amine is from about 1:0.5 to 1:50.

5. A method according to claim 1 wherein the mole ratio of said nitroketone to said amine is from about 1:05 to 1:5.

6. A method according to claim 1 wherein the mole ratio of said nitroketone to said alkanoic acid anhydride is from about 1:1 to about 1:20.

7. A method according to claim 1 wherein said tertiary amine has from 3 to 36 carbons.

8. A method according to claim 1 wherein said tertiary amine is pyridine.

9. A method according to claim 1 wherein said tertiary amine is quinoline.

10. A method according to claim 1 wherein said tertiary amine is triethylamine.

11. A method according to claim 1 wherein said alkanoic acid anhydride is acetic anhydride.

12. A method according to claim 1 wherein said nitroketone is 1-nitro-2-hexadecanone.

13. A method according to claim 1 wherein step (b) is conducted at a temperature of from about 80° to 100° C.

14. A method according to claim 1 wherein said non-oxidizing inorganic acid is hydrochloric acid.

15. A method according to claim 1 wherein said non-oxidizing inorganic acid is sulfuric acid.

16. A method according to claim 1 wherein said non-oxidizing inorganic acid is phosphoric acid.

17. A method according to claim 1 wherein said non-oxidizing organic acid is methanesulfonic acid.

18. A method according to claim 1 wherein said non-oxidizing organic acid is p-toluenesulfonic acid.

19. A method according to claim 1 wherein the mole ratio of said non-oxidizing acid to said alkenoic acid is from about 0.1:1 to 20:1.

20. A method according to claim 1 wherein step (b) is conducted in the presence of a non-reactive polar organic solvent having a boiling point of about 80° C. to about 180° C.

21. A method according to claim 13 wherein said solvent is dioxane.

22. A method according to claim 1 wherein said 2-oxoalkanoic acid is 2-oxohexadecanoic acid.

23. A method for the preparation of a 2-alkanoyloxy-2-alkenoic acid which comprises contacting an alpha-nitroketone with an alkanoic acid anhydride and a tertiary amine.

24. A method according to claim 23 wherein said contacting is at a temperature of from about room temperature to 150° C.

25. A method according to claim 23 wherein said contacting is at a temperature of from about 90° to 150° C. and where an alkylnitrile coproduct is formed.

26. A method according to claim 23 wherein the mole ratio of said nitroketone to said amine is from about 1:0.5 to 1:50.

27. A method according to claim 23 wherein the mole ratio of said nitroketone to said amine is from about 1:05 to 1:5.

28. A method according to claim 23 wherein the mole ratio of said nitroketone to said alkanoic acid anhydride is from about 1:1 to 1:20.

29. A method according to claim 23 wherein said tertiary amine has from 3 to 36 carbons.

30. A method according to claim 23 wherein said alkanoic acid anhydride is acetic anhydride.

31. A method according to claim 23 wherein said tertiary amine is pyridine.

32. A method according to claim 23 wherein said tertiary amine is quinoline.

33. A method according to claim 23 wherein said tertiary amine is triethylamine.

34. A method according to claim 23 wherein said 2-alkanoyloxy-2-alkenoic acid is 3-ethanoyloxy-2-hexadecenoic acid.

35. A method according to claim 25 wherein said nitrile is pentadecanonitrile.

* * * * *